Feb. 7, 1967 H. C. SWIM ET AL Plant Pat. 2,710
ROSE PLANT
Filed Nov. 22, 1965
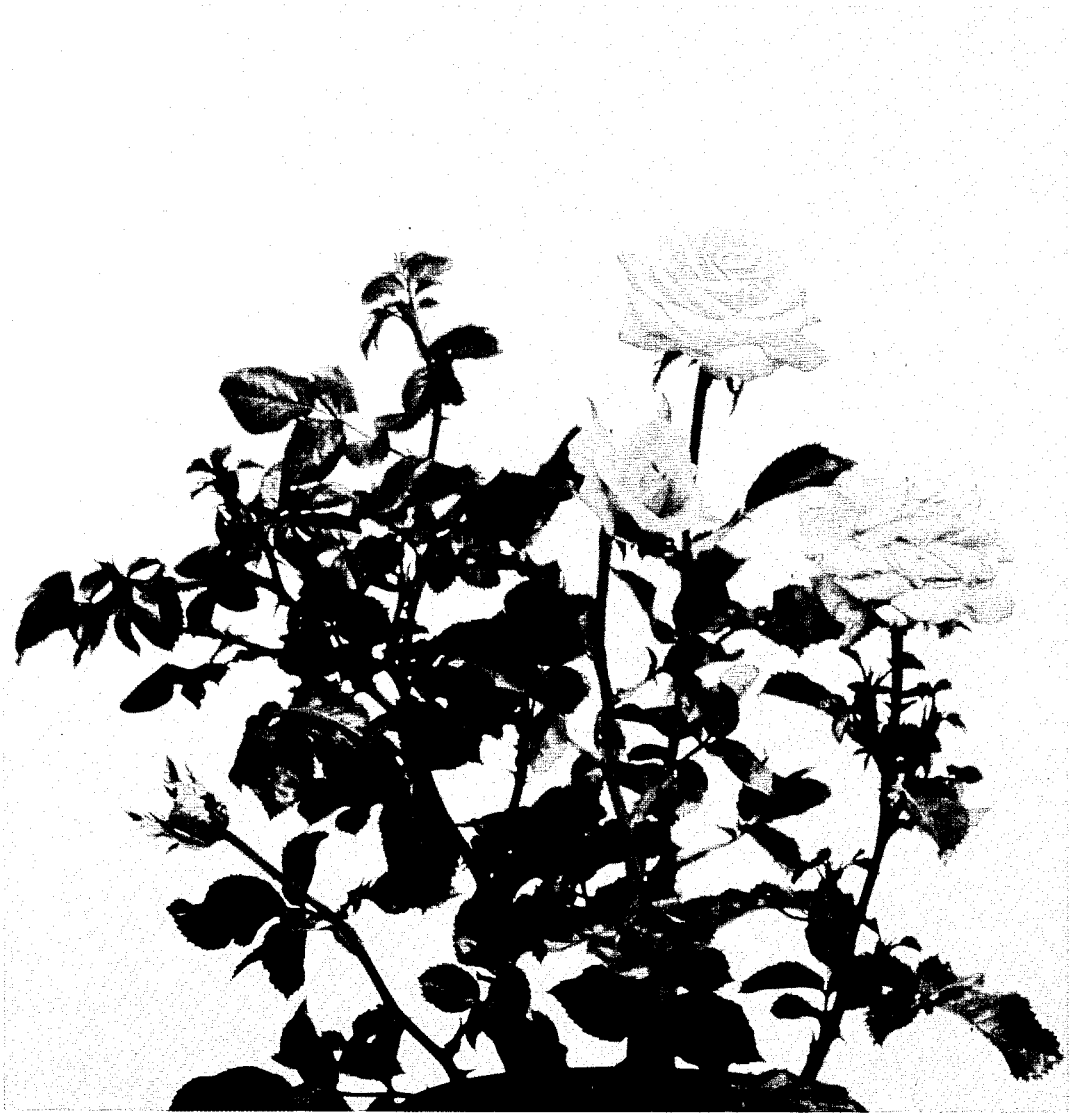
Inventors.
H. C. Swim
O. L. Weeks
By: Robb & Robb
Attorneys.

United States Patent Office

Plant Pat. 2,710
Patented Feb. 7, 1967

2,710
ROSE PLANT

Herbert C. Swim, Ontario, and O. L. Weeks, Chino, Calif., assignors to Swim and Weeks, Chino, Calif., a copartnership consisting of Herbert C. Swim and O. L. Weeks Filed Nov. 22, 1965, Ser. No. 509,229
1 Claim. (Cl. Plt.—25)

The present invention relates to a new and distinct variety of rose plant of the floribunda class, which was originated by us by crossing an unnamed and unpatented seedling of "Circus" (Plant Patent No. 1,382) × "Garnette" (unpatented) with the variety known as "Spartan" (Plant Patent No. 1,357).

As the result of this breeding, we have produced a new and improved rose variety having the following unique combination of characteristics which are outstanding therein and which distinguish it from its parents, as well as from all other varieties of which we are aware:

(1) A tall, upright and vigorous habit of growth, with cutting stems of good length when grown under greenhouse conditions;

(2) A pronounced reddish-purple color of the new growth and prickles;

(3) A more or less continuous production of flowers when grown under either greenhouse or garden conditions;

(4) A distinctive and attractive shape of the buds and flowers substantially as described and illustrated;

(5) A relatively small bud and flower size, with good flower petalage;

(6) Long lasting qualities of the flowers both on the plant and when cut; and (7) A distinctive and attractive general color tonality of the flowers ranging between Strong Yellowish-Pink and Strong Reddish-Orange in the newly open flowers and becoming near Strong Reddish-Orange as the flowers mature.

In comparison with its unnamed seed parent, the new variety is upright in its habit of growth, instead of spreading; its stems are distinctively angled in appearance similar to those of "Garnette" and unlike the stems of the seed parent which show little evidence of this trait; the flowers have greater petalage and have substantially greater substance and lasting qualities; and the flower color may be generally described as orange instead of the typical bi-color of the seed parent in which the inner petal surfaces are bright yellow at the base and bright red over the remainder, while the reverse surface is dominantly deep pink.

As compared with its pollen parent, "Spartan," the new variety is both distinctly upright and quite tall in its habit of growth while the parent is neither; the stems are distinctively angled but not found to any degree in this parent; the new growth is reddish-purple in color to a pronounced degree, while "Spartan" has only a small amount of this pigment in its new growth; at the cutting stage, the flower buds are long-pointed to urn-shaped instead of short-pointed like those of this parent; the flowers are smaller in size; and the flowers have greater petalage.

Asexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Maryland, except where general color terms of ordinary dictionary significance are obvious:

Type: Tall; bush; greenhouse; seedling; for cut flowers.
Class: Floribunda.
Breeding: Seedling.
*Seed parent.*—An unnamed, seedling of "Circus" × "Garnette."
*Pollen parent.*—"Spartan."
Propagation: Holds its distinguishing characteristics through succeeding propagations by budding.

*Flower*

Locality where grown and observed: Ontario, California.
Flowers borne: From singly to several to stem; in irregular clusters; on strong, long stems.
Quantity of bloom: Abundant, in greenhouse.
Continuity: More or less continuous.
Fragrance: Very slight.
Bud:
*Peduncle.*—Medium length; from medium to heavy caliper; erect; stiff; smooth except for many stiff stipitate glands. Color—yellowish-green on unexposed side and reddish-purple on exposed side.
*Before calyx breaks.*—Size—from medium to small. Form—short; pointed; no neck; with foliaceous appendages on the surface of the bud; with foliaceous parts extending beyond the tip of the bud equal to ¼ of its length and occasionally more. Color—near Deep Pink, Plate 2.5R 6/11.
*As calyx breaks.*—Color—deep Yellowish-Pink, Plate 5R 6/11, except at apex which becomes near Vivid Red, Plate 5R 5/13.
*As first petal opens.*—Size—small. Form—long; from pointed to ovoid to urn-shaped. Color: outside—Deep Yellowish-Pink, Plate 5R 6/11, except around point of attachment which is greenish-white; inside—near Strong Reddish-Orange, Plate 7.5R 6/12, except at base where color around point of attachment is greenish-yellow.
*Opening.*—Opens up well.
Bloom:
*Size (when fully open).*—Small; from 2 inches to 2¼ inches.
*Petalage.*—From double to very double; usually with no stamens showing; from 35 to 40 petals; arranged more or less regularly.
*Form.*—High-centered at first and remaining high-centered; petals being at first loosely rolled outward, but later becoming more tightly rolled outward at maturity.
Petals:
*Texture.*—Thick; leathery.
*Appearance.*—Inside—crepe-like. Outside—shiny.
*Shape.*—Outside—about ½ wider than long, with apex rounded. Intermediate—nearly round, with apex entire and rounded. Inside—broadly ovate, with apex entire and rounded.

This description of a newly opened flower was made from a rose grown outdoors during the month of October at Ontario, California:

*Color.*—Outer petal: outside surface—small area of greenish-white about point of attachment, with remainder of petal between Strong Yellowish-Pink, Plate 5R 7/9 and Deep Yellowish-Pink, Plate 5R 6/11 to Deep Pink, Plate 2.5R 6/11; inside surface—small area about point of attachment near Brilliant Greenish-Yellow, Plate 7.5Y 9/8, with remainder between Strong Yellowish-Pink, Plate 7.5R 7/9 and Strong Reddish-Orange, Plate 7.5R 6/12. Intermediate petal: outside surface—small area about point of attachment greenish-white, with remainder ranging from Deep Pink, Plate 2.5R 6/11 through Deep Yellowish-Pink, Plate 5R 6/11 to Strong Yellowish-Pink, Plate 5R 7/9; inside surface—small area about point of attachment near Brilliant Greenish-Yellow, Plate 7.5Y 9/8, with remainder of petal ranging from near Deep Yellowish-Pink, Plate 5R 6/11 at apex through Strong Reddish-Orange, Plate 7.5R 6/12 to near Strong Reddish-Orange, Plate 7.5R 5/13. Inner petal: outside surface—base near Brilliant Greenish-Yellow, Plate 7.5Y 9/8, often extending along midrib to apex, with remainder between Deep Pink, Plate 2.5R 6/11 and Vivid Red, Plate 5R 5/13; inside surface—base near Brilliant Yellow, Plate 5Y 9/9, with remainder ranging from Deep Yellowish-Pink, Plate 5R 6/11 through Strong Reddish-Orange, Plate 7.5R 6/12 to near Strong Reddish-Orange, Plate 7.5R 5/13, and with Yellow color of base sometimes extending partly or all the way to apex along midrib.

This description was made from a rose that was open for three days outdoors during the month of October at Ontario, California:

*Color.*—Outer petal: outside surface—base Brilliant Greenish-Yellow, Plate 7.5Y 9/8, with remainder from Moderate Pink, Plate 2.5R 8/5 and Strong Yellowish-Pink, Plate 5R 7/9 to near Deep Yellowish-Pink, Plate 5R 6/11; inside surface—base Brilliant Greenish-Yellow, Plate 7.5Y 9/8, with remainder between Deep Yellowish-Pink, Plate 5R 6/11 and Strong Reddish-Orange, Plate 7.5R 6/12. Inner petal: outside surface—base near Brilliant Greenish-Yellow, Plate 7.5Y 9/8, sometimes extending to various lengths along midrib, with remainder between Strong Yellowish-Pink, Plate 5R 7/9 and Deep Yellowish-Pink, Plate 5R 6/11; inside surface—base Brilliant Greenish-Yellow, Plate 7.5Y 9/8, with remainder between Strong Reddish-Orange, Plate 7.5R 6/12 and Strong Yellowish-Pink, Plate 7.5R 7/9.

*General color effect.*—Newly opened flower—between Strong Yellowish-Pink, Plate 7.5R 7/9 and Strong Reddish-Orange, Plate 7.5R 6/12. 3-days open—Near Reddish-Orange, Plate 7.5R 6/12.

*Behavior.*—Persist.

*Flower longevity.*—On bush in garden—6 days in October. Cut roses grown outdoors and kept at livingroom temperature—7 days in October.

*Reproductive organs*

Stamens: From few to medium quantity; arranged irregularly, partly about pistils and mixed with petaloids.

Filaments: From medium length to long; most with anthers. Color—greenish-yellow at base and pale pink at apex.

Anthers: Small; open at various times. Color—yellow.

Pollen: From sparse to moderate quantity. Color—gold.

Pistils: Medium quantity.

Styles: Very uneven; from medium length to long; loosely separated; somewhat twisted. Color—reddish-purple, with progressively greater intensity toward apex.

Stigma: Color—white.

Ovaries: All protruding from calyx.

Hips: None observed; does not regularly set hips.

Sepals: Permanent until peduncle falls; straight; spear-shaped except for some foliaceous appendages.

Seeds: None observed.

*Plant*

Foliage:

*Leaves.*—Compound of 3 to 7 leaflets; moderately abundant; medium size; medium thickness; moderately hard; semi-glossy.

*Leaflets.*—Shape—terminals ovate-cuneate and laterals ovate. Apex—acute. Base—base of laterals round and base of terminals cuneate. Margin—both simply and doubly serrate.

*Color.*—Mature: upper surface—very dark green; under surface—veins dark green, with light green between veins. Young: upper surface—reddish-purple, except sometimes along midrib and on lower lateral leaflets which are dark green; under surface—interstices light green, with veins and margins reddish-purple.

*Rachis (the supporting stem of the compound leaf).*—From light to medium weight. Upper side—grooved; ridges regularly lined with stipitate glands. Under side—smooth, except for occasional stipitate glands.

*Stipules.*—Moderately short; moderately narrow; with short points turning out at an angle of 45°.

*Disease resistance.*—Relatively medium to good resistance to powdery mildew when grown outdoors, as determined by comparison with many other rose varieties grown under comparable cultural conditions at Ontario, California.

Growth:

*Habit.*—Tall; bushy; upright; much-branched.

*Growth.*—Very vigorous.

*Canes.*—Medium caliper, but stiff and zig-zagging to form angles in stem at each leaf node.

*Main stems.*—Color—dark dull olive green. Large prickles—several; medium length; straight; with short, medium broad base; color—brown. Small prickles—few; color—brown. Hairs—none.

*Branches.*—Color—bright green. Large prickles—several; medium length; nearly straight; with short base of medium width; color—brown. Small prickles—few; color—brown. Hairs—none.

*New shoots.*—Color—reddish-purple. Large prickles—from short to medium length; slightly hooked downward; with narrow base of short to medium length; color—reddish-purple. Small prickles—few; color—reddish-purple. Hairs—none.

We claim:

A new and distinct variety of rose plant of the floribunda class, substantially as herein shown and described, characterized particularly as to novelty by the unique combination of a tall, upright and vigorous habit of growth, with cutting stems of good length when grown under greenhouse conditions, a pronounced reddish-purple color of the new growth and prickles, a more or less continuous production of flowers when grown under either greenhouse or garden conditions, a distinctive and attractive shape of the buds and flowers substantially as described and illustrated, a relatively small bud and flower size, with good flower petalage, long lasting qualities of the flowers both on the plant and when cut, and a distinctive and attractive general color tonality of the flowers ranging between Strong Yellowish-Pink and Strong Reddish-Orange in the newly open flowers and becoming near Strong Reddish-Orange as the flowers mature.

No references cited.

ABRAHAM G. STONE, *Primary Examiner.*

R. E. BAGWILL, *Assistant Examiner.*